US009872742B1

(12) United States Patent
Albarakati et al.

(10) Patent No.: US 9,872,742 B1
(45) Date of Patent: Jan. 23, 2018

(54) ORTHODONTIC HAND INSTRUMENT

(71) Applicant: KING SAUD UNIVERSITY, Riyadh (SA)

(72) Inventors: Sahar Faisal Albarakati, Riyadh (SA); Bader Khalid Albalkhi, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/384,177

(22) Filed: Dec. 19, 2016

(51) Int. Cl.
A61C 3/00 (2006.01)
A61C 7/02 (2006.01)

(52) U.S. Cl.
CPC .................................. A61C 7/026 (2013.01)

(58) Field of Classification Search
CPC ...................................................... A61C 7/026
USPC .................. 433/141–147, 136, 3–24; 254/25
See application file for complete search history.

(56) References Cited

U.S. PATENT DOCUMENTS

| 4,167,063 | A | | 9/1979 | Sosnay | |
|---|---|---|---|---|---|
| 4,836,781 | A | * | 6/1989 | Meinershagen | A61C 5/125 433/141 |
| D687,553 | S | | 8/2013 | Coreil | |
| 2006/0063123 | A1 | | 3/2006 | Cleary et al. | |
| 2006/0121405 | A1 | | 6/2006 | Hollard et al. | |
| 2009/0286199 | A1 | * | 11/2009 | Creasman | A61C 3/00 433/141 |

FOREIGN PATENT DOCUMENTS

GB   2 451 460 A   2/2009

OTHER PUBLICATIONS

"Double Ended Tucker," https://dbortho.com/collections/orthodontic-instruments/products/double-ended-tucker (Accessed on Nov. 9, 2016) 2pgs.
"New Dental Tucker Ligature Double Ended Lab Instrument CE," http://www.ebay.com/itm/New-Dental-Tucker-Ligature-Double-Ended-Lab-Instrument-CE-141693283354?hash=item20fd93ecla:g:NgwAAOSwstxVffcF (Accessed on Nov. 9, 2016) 1pg.

* cited by examiner

Primary Examiner — Yogesh Patel
(74) Attorney, Agent, or Firm — Richard C. Litman

(57) ABSTRACT

The orthodontic hand instrument includes a handle portion having a first end and an opposing second end, as well as a first shaft extending outward from the first end and a second shaft extending outward from the second end, each shaft having a working end. The working end of each shaft includes a stoop having a gingival head and an occlusal head, and a vertical slot extending between the gingival head and the occlusal head. Both the gingival head and the occlusal head of the stoop of each working end have a rectangular shape. The handle portion may have a knurled surface or other suitable griping surface for preventing the hand instrument from slipping out of the orthodontist's hand. Further, each shaft can include a tapered portion adjacent to the corresponding working end.

6 Claims, 4 Drawing Sheets

ORTHODONTIC HAND INSTRUMENT

BACKGROUND OF THE INVENTION

1. Field of the Invention

The present invention relates to orthodontic hand tools, and particularly to an orthodontic hand instrument used for making distal cinch back bends on dental arch wires so that the ends of the arch wire are flush with the molar band tube.

2. Description of the Related Art

During orthodontic treatment, particularly the during the late stages of installing a fixed orthodontic appliance, large diameter arch wires are used, e.g., to correct the curvature of the patient's teeth. Once inserted into the respective molar band tube, the arch wires require cinching back flush to the distal end of the molar band tube so that the arch wires maintain the orthodontic appliance fixed in place and do not damage the patient's mouth. Currently, there are various orthodontic pliers (e.g., the Weingart pliers, the Nickel Titanium Distal Cinch Back pliers, and the How pliers) that can be used to cinch back the small diameter arch wire once the procedure is complete. For example, after grasping the small diameter arch wire, the pliers allow the orthodontist to cinch the arch wire(s) intraorally behind the buccal tube.

However, none of these pliers provide an easy, safe, and effective means for cinching back large diameter arch wire(s) in a satisfactory manner, without leaving a space between the gingival bend and the distal end of the molar band tube, which can result in unfavorable tooth and arch movement when the bend is not flush. This is especially true during the late stages of treatment, when utilization of large diameter rectangular arch wires is most prevalent. Another drawback associated with the utilization of the currently available pliers concerns patient discomfort. For example, it is difficult to control the bend of the distal end of the arch wire in patients having small mouths. Such difficulty in controlling and grasping the arch wire can lead to slippage of the pliers within the patient's mouth. This, in turn, can lead to scraped gums, along with other types of discomfort and dissatisfaction on the part of the patient.

Additionally, the double ended orthodontic ligature director is one type of dental hand instrument that is used to direct arch wires into the bracket slots during retie procedures to push steel ligatures into difficult areas to engage the bracket tie-wings and to push open the coil when placing split hooks. Despite having two ends, each having a notched serrated tip, one of which is angled for tucking ligatures, the double ended orthodontic ligature director is unreliable when it comes to cinching back large diameter arch wires, since the serrated tip breaks often. The Double-Ended Distal-End Bender is another type of dental hand instrument used to direct arch wires. However, despite having two ends with two openings of different diameters, the Double-Ended Distal Bender does not allow for the cinching back of the large diameter arch wire flush behind the distal end of the molar band tube.

Thus, an orthodontic hand instrument solving the aforementioned problems is desired.

SUMMARY OF THE INVENTION

The orthodontic hand instrument includes a handle portion having a first end and an opposing second end, as well as a first shaft extending outward from the first end and a second shaft extending outward from the second end, each shaft having a working end. The working end of each shaft includes a stoop having a gingival head and an occlusal head, and a vertical slot extending between the gingival head and the occlusal head. Both the gingival head and the occlusal head of the stoop of each working end have a rectangular shape. The handle portion may have a knurled surface or other suitable griping surface for preventing the hand instrument from slipping out of the orthodontist's hand. Further, each shaft can include a tapered portion adjacent to the corresponding working end.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1A:
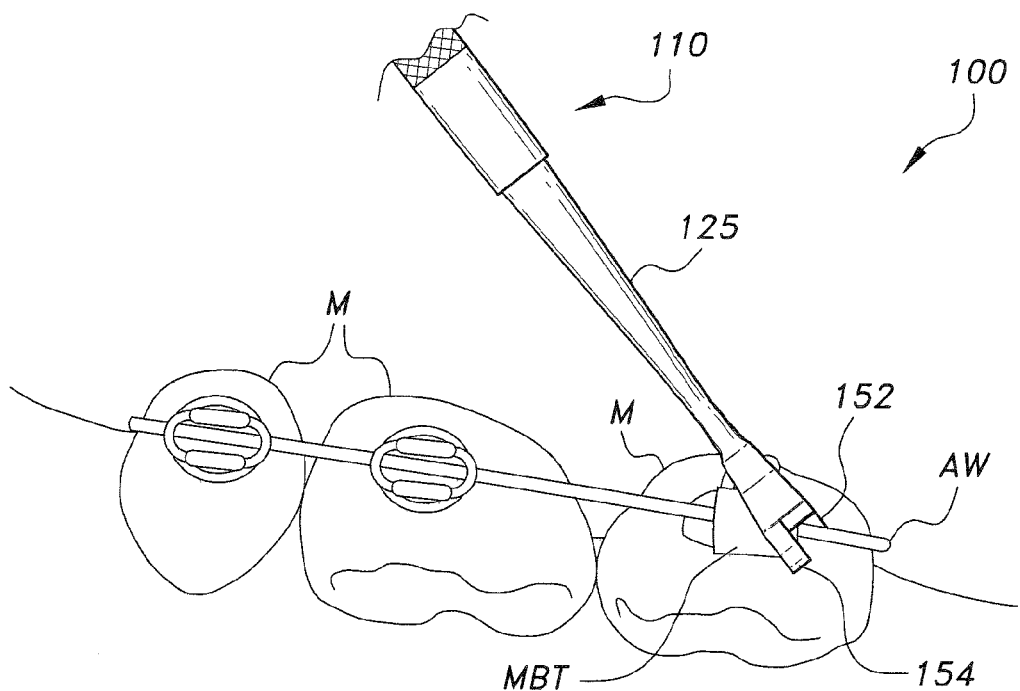
FIG. 1A is a partial environmental perspective view of an orthodontic hand instrument according to the present invention, shown with the working end positioned on an arch wire protruding from a molar band tube in the upper right quadrant.
Figure 1B:
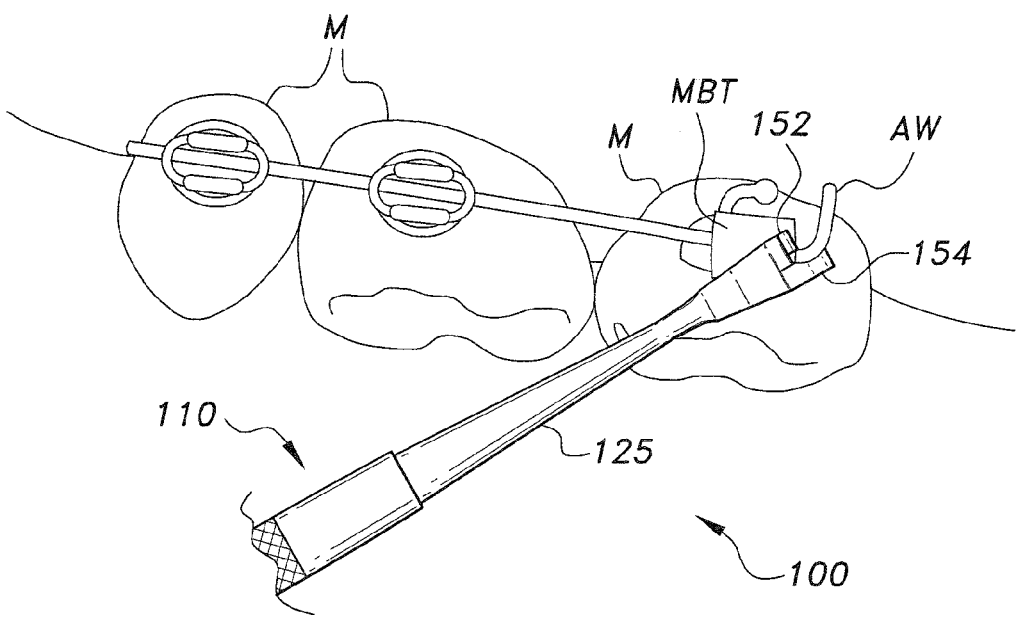
FIG. 1B is a partial environmental perspective view of the orthodontic hand instrument of FIG. 1A, shown cinching back the arch wire protruding from the molar band tube in the upper right quadrant.

Referring to FIGS. 1A and 1B, the orthodontic hand instrument 100 enables an orthodontist to make flush, distal cinch back bends of arch wire(s), especially large diameter arch wire(s) AW used for the installation of a fixed orthodontic appliance, that extend from the distal end of the molar band tube MBT. The hand instrument 100 is configured for enabling a quick, easy, and convenient manner in which to cinch back the portion of the arch wire AW protruding from the molar band tube MBT without deforming or breaking the hand instrument 100, interfering with molar bracket bonding, or leaving a space between the bend and distal end of the molar band tube MBT.

Figure 2:
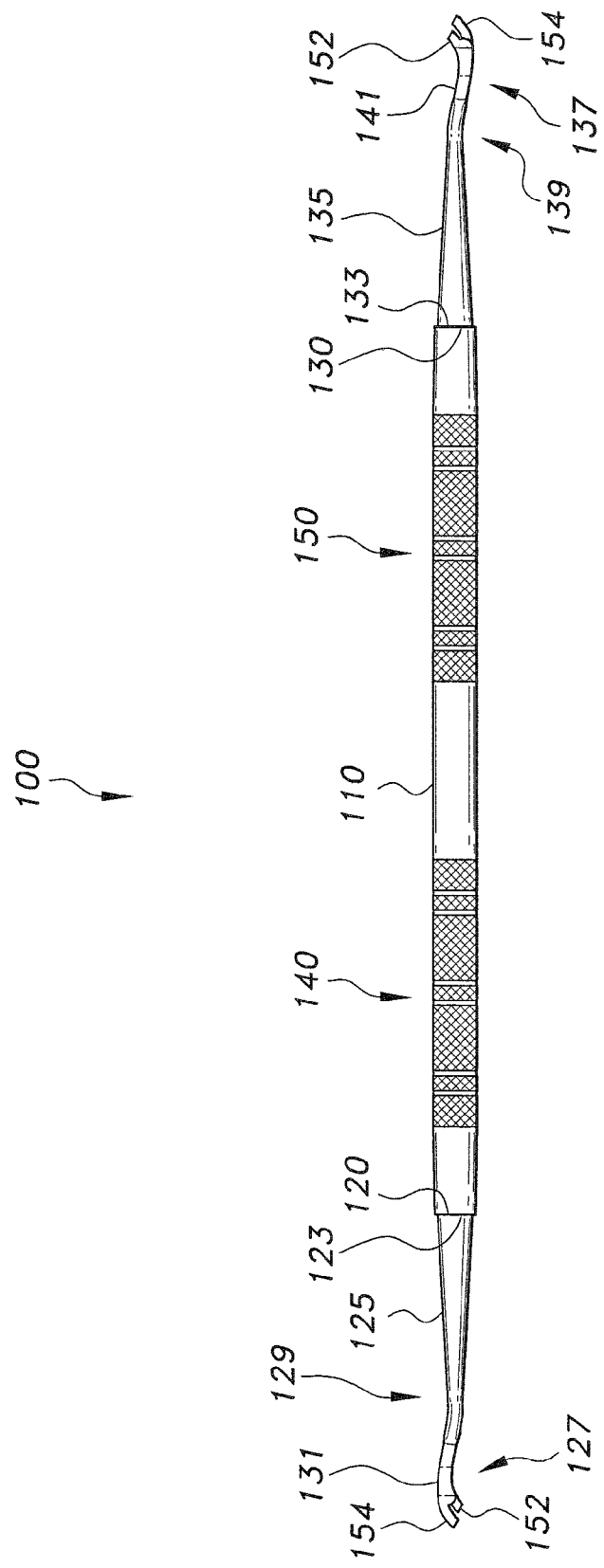
FIG. 2 is a side view of an orthodontic hand instrument according to the present invention.

Referring to FIG. 2, the hand instrument 100 includes a handle portion 110 having a first end 120 and an opposing second end 130. A first shaft 125 having a working end 127 and a second shaft 135 having a working end 137 extend outward from the first end 120 and the second end 130, respectively, of the handle portion 110. The first shaft 125 has a proximal end 123, opposite the working end 127, rigidly fixed to the first end 120 of the handle portion 110. Similarly, the second shaft 135 has a proximal end 133, opposite the working end 137, rigidly fixed to the second end 130 of the handle portion 110. Further, the first shaft 125 includes a tapered portion 129 positioned between the proximal end 123 and the working end 127. Similarly, the second shaft 135 also includes a tapered portion 139 positioned between the proximal end 133 and the working end 137.

The hand instrument 110, as well as each shaft 125, 135 can be formed from any suitable medical grade metallic material, such as stainless steel or a nickel-titanium alloy, that can provide a high degree of wear resistance so that the hand instrument 100 can function properly for extended periods of time. The handle portion 110 includes an elongated, rigid handle that can have any suitable shape, such as a substantially cylindrical shape, so that the handle portion 110 of the hand instrument 100 is comfortable within the hand of the orthodontist or other person using the hand instrument 100. The handle portion 110 can have any suitable length, such as a length of about 10 cm, and can have any suitable diameter, such as a diameter of about 5 mm. Further, the handle portion 110 may include at least one knurled portion, such as a first knurled surface 140 and a second knurled surface 150, or other suitable gripping surface configured for preventing the hand instrument 100 from slipping out of the orthodontist's hand.

Figure 3:
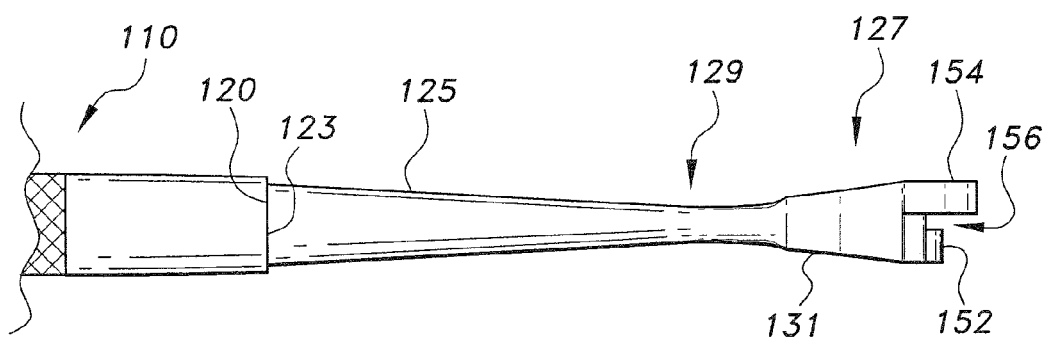
FIG. 3 is a partial top view of the orthodontic hand instrument of FIG. 2, showing details of the working end.
Figure 4:
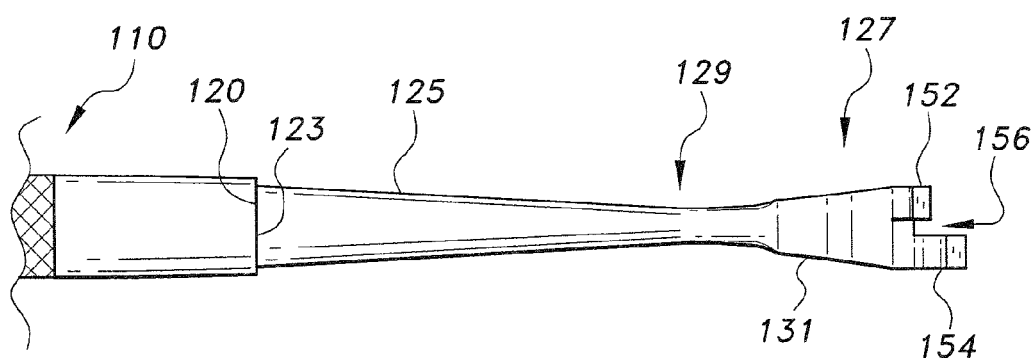
FIG. 4 is a partial bottom view of the orthodontic hand instrument of FIG. 2, showing details of the working end.
Figure 5:
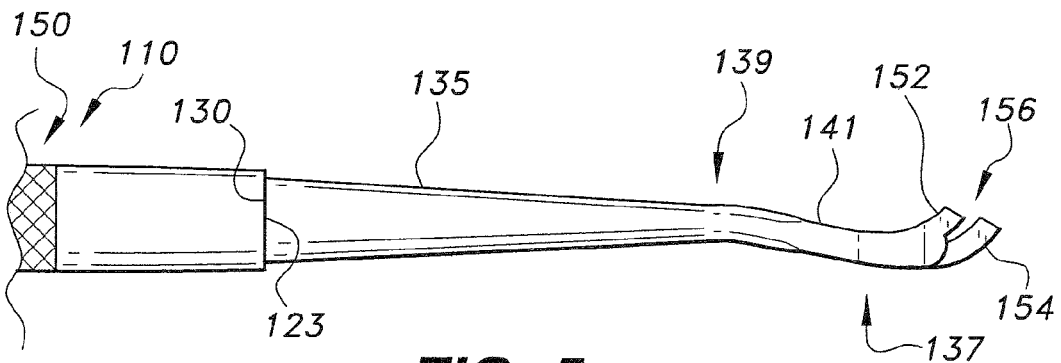
FIG. 5 is a side view of the second shaft of the orthodontic hand instrument of FIG. 2.
Figure 6:
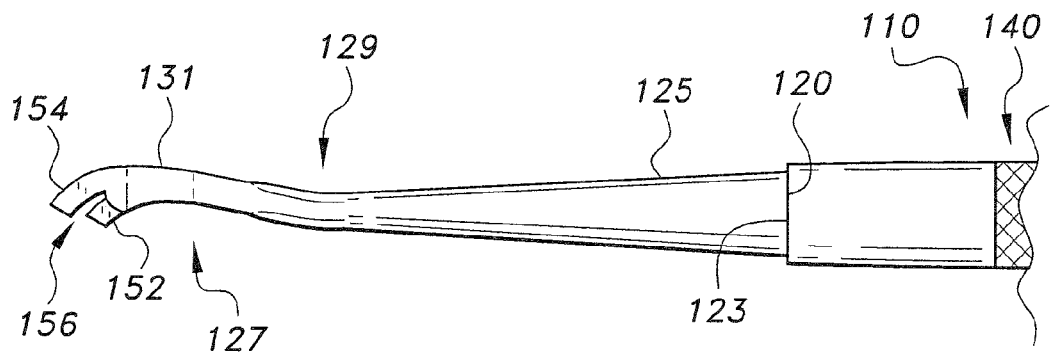
FIG. 6 is a side view of the first shaft of the orthodontic hand instrument of FIG. 2.
Figure 7:
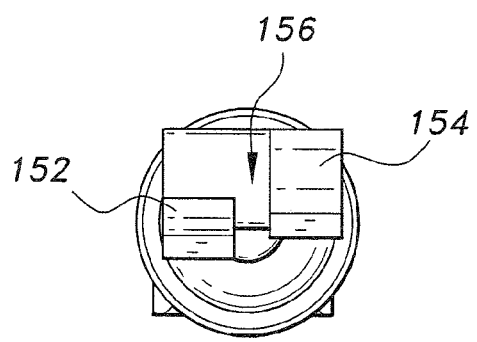
FIG. 7 is an end view of the orthodontic hand instrument of FIG. 2.

As shown in FIGS. 3, 4, and 6, the working end 127 of the first shaft 125 includes a stoop 131 or bent portion. Similarly, as shown in FIG. 5, the working end 137 of the second shaft 135 includes a stoop 141 or bent portion. Each stoop 131, 141 has a bifurcated end including a gingival head 152 and an occlusal head 154, the occlusal head 154 projecting beyond the gingival head 152. As seen most clearly in FIGS. 2 and 6, the stoop 131 at the end of the first shaft 125 has a slight upward bend at the junction of the tapered end 129 and the proximal end of the stoop 131, and a more pronounced downward bend adjacent the heads 152, 154. Similarly, as seen most clearly in FIGS. 2 and 5, the stoop 141 at the end of the second shaft 135 has a slight downward bend at the junction of the tapered end 139 and the stoop 141, and a more pronounced upward bend adjacent the heads 152, 154. It will also be noted that the orientation of the gingival head 152 and the occlusal heads 154 are reversed 180° at opposite ends of the handle 110, i.e., the working ends 127 and 137 are mirror images of each other, for a purpose described below. Each head 152, 154 has a substantially rectangular shape, and may have any suitable dimensions, such as a length of about 1 mm, a height of about 1 mm, and a width W of about 2 mm (FIG. 7). Similar to the handle portion 110 and each shaft 125,135, the gingival head 152 and the occlusal head 154 of each stoop 131,141 can be formed from any suitable type of medical grade metallic material, such as stainless steel or a nickel-titanium alloy. Further, as shown in FIG. 7, each stoop 131, 141 has a vertical slot 156 measuring about 1 mm extending between each head 152,154. Once the arch wire AW is positioned within the vertical slot 156 of a respective excavator portion 131, 141, the hand instrument 100 allows for manipulating the arch wire AW, including upward and downward movement, as well as forming the sharp bend of the large (and small) diameter arch wire AW extending from the molar band tube MBT so that the arch wire AW is flush with the distal end of the molar band tube MBT, as further discussed below.

The first shaft 125 is positioned such that each head 152,154 of the stoop 131 of the working end 127 faces a given direction, such as a downward direction (in the orientation shown in FIG. 2). The second shaft 135, on the other hand, is positioned such that each head 152,154 of the excavator portion 141 of the working end 137 faces a direction opposite the given direction, such as an upward direction (in the orientation shown in FIG. 2). Depending on which quadrant of the mouth the orthodontist is working, he/she can utilize the working end 127 of the first shaft 125 or the working end 137 of the second shaft 135 for cinching the arch wire AW, having a diameter of less than 0.0003 inches, extending from the molar band tube MBT. It is to be noted that each head 152,154 of each excavator portion 131, 141 is designed so as to allow easy manipulation of the arch wire AW to effectuate a gingivally directed bend (i.e., an upward bend for upper arch wire and/or a downward bend for lower arch wire) of the large diameter arch wire AW protruding from each molar band tube MBT, so that the arch wire(s) AW is flush with the distal end of the molar band tube MBT.

Each shaft 125,135 has a circular cross-sectional configuration and a smooth non-interrupted exterior surface. Further, each shaft 125,135 can have any suitable length, such as a length of about 35 mm from the proximal end 123,133 of the corresponding shaft 125,135 to the occlusal head 154 of each shaft 125,135. The length between the proximal end 123 and the tapered portion 129 of the first shaft 125, as well as the length between the proximal end 133 and the tapered portion 139 of the second shaft 135, however, is about 20 mm, and the distance between the tapered portion 129,139 of each shaft 125,135 and the corresponding occlusal head 154 of each shaft 125,135 is about 15 mm. It is to be noted that the length between the tapered portion 129,139 and the head portion of each shaft 125,135, is about 10 mm, with each head portion having a length of about 5 mm.

As illustrated in FIGS. 2, 5, and 6, the working end 127,137 of each shaft 125, 135 extends outward from the tapered portion 129,139 of each shaft 125,135 at an angle of about 45°. For example, the working end 127 of the first shaft 125 extends upward at an angle of about 45° from the tapered portion 129 of the first shaft 125 and the working end 137 of the second shaft 135 extends downward at an angle of about 45° from the tapered portion 139 of the second shaft 135. Further, each head portion extends at a 120° angle from each working end 127,137. For example, the head portion of the working end 127 of the first shaft 125 extends downward at an angle of about 120° and the head portion of the working end 137 of the second shaft 135 extends upward at an angle of about 120° so that one working end 127, 137 can be used to cinch back the arch wire AW extending from the upper right and lower left molar band tube MBT, while the other working end 127, 137 can be used to cinch back the arch wire AW extending from the lower right and upper left band tube MBT.

It is to be understood that during fixed orthodontic treatment, the molar band tubes MBT and the arch wire(s) AW are considered part of the orthodontic appliance. By way of operation, first molar band tubes MBT are cemented onto the upper and lower molars M. Typically, the molar band tubes MBT are placed buccally. The small, or more commonly, the large diameter arch wire AW is then threaded through these molar band tubes MBT to maintain the alignment of the person's teeth. After the arch wire AW is secured in place, any excess arch wire AW projecting distally from the molar tube MBT is cut. However, despite being cut, there is typically about 3 mm of arch wire AW remaining, as illustrated in FIG. 1A. The patient is asked to open his/her mouth slightly to allow one of the shafts, such as the shaft 125 or the shaft 135 of the hand instrument 100, to fit into the buccal vestibule. It is to be noted that the wider the patient opens his/her mouth, the harder it is to reach the arch wire AW, since opening wide brings the anterior border of the mandibular ramus forward and blocks the buccal vestibular accessibility to the molar tubes MBT.

Once the buccal vestibule is made accessible to the orthodontist, the orthodontist may utilize one of the working ends 127, 137 of the hand instrument 100 to grasp the arch wire AW by positioning the arch wire AW within the vertical slot 156 between the gingival head 152 and the occlusal head 154 of the respective excavator portion 131,141 of the shaft 125,135 being used. The gingival head 152 is always oriented gingivally (towards the gums) and the occlusal head 154 is always oriented occlusally (towards the bite surface of the teeth) when gripping the arch wire, with the gingival head in contact with the distal end of the molar buccal tube MBT holding the arch wire AW and occlusal head in contact with the projecting end of the arch wire AW. It is to be noted that the orthodontist can hold the hand instrument 100 in a manner similar to holding a pencil to access the distal projection of the arch wire AW. The mesial aspect of the gingival head 152 is used to grasp the inner surface of the arch wire AW at a point on the arch wire AW that will allow intimate contact with the distal end of the molar band tube MBT, with the occlusal head 154 grasping the outer surface of the projecting arch wire AW (FIG. 1A). While the arch wire AW is in the vertical slot 156, the occlusal head 154 is moved across the arch wire AW toward the surface of the gingival head 152, thereby producing the required gingival bend at a sharp angle and flush to the distal end of the molar ban tube MBT, as illustrated in FIG. 1B. These cinch bends are utilized for securing or looping the large diameter arch wire(s) AW to prevent the flaring or backwards movement of the proclined teeth.

It is to be understood that the present invention is not limited to the embodiments described above, but encompasses any and all embodiments within the scope of the following claims.

We claim:

1. An orthodontic hand instrument configured for making distal cinch back bends on dental arch wires, comprising:
    a handle portion having a first end and an opposing second end;
    a first shaft extending from the first end of the handle portion, the first shaft having a tapered distal end;
    a first stoop extending from the tapered distal end of the first shaft, the first stoop having a bifurcated head portion defining a rectangularly-shaped gingival head having a length of about 1 mm, a height of about 1 mm and a width of about 2 mm, a rectangularly-shaped occlusal head having a length of about 1 mm, a height of about 1 mm and a width of about 2 mm overlying and projecting beyond the gingival head, and a 1 mm vertical slot between the gingival head and the occlusal head, the slot being dimensioned and configured for engaging an arch wire of a dental appliance;
    a second shaft extending from the second end of the handle portion, the second shaft having a tapered distal end; and
    a second stoop extending from the tapered distal end of the second shaft, the second stoop having a bifurcated head portion defining a rectangularly-shaped gingival head having a length of about 1 mm, a height of about 1 mm and a width of about 2 mm, a rectangularly-shaped occlusal head having a length of about 1 mm, a height of about 1 mm and a width of about 2 mm overlying and projecting beyond the gingival head, and a 1 mm vertical slot between the gingival head and the occlusal head, the slot being dimensioned and configured for engaging an arch wire of a dental appliance, the second stoop being a mirror image of the first stoop.

2. The orthodontic hand instrument according to claim 1, wherein the handle portion includes at least one knurled surface configured for enhancing an orthodontist's grip on the handle.

3. The orthodontic hand instrument according to claim 1, wherein the handle portion has a length of about 10 cm and a diameter of about 5 mm.

4. The orthodontic hand instrument according to claim 1, wherein each said first stoop and said second stoops have bends extending in opposite directions.

5. The orthodontic hand instrument according to claim 1, wherein the instrument is made from stainless steel.

6. The orthodontic hand instrument according to claim 1, wherein the instrument is made from a nickel-titanium alloy.

\* \* \* \* \*